(12) United States Patent
Wei

(10) Patent No.: US 7,647,094 B2
(45) Date of Patent: Jan. 12, 2010

(54) METHOD FOR DERIVING STANDARD 12-LEAD ELECTROCARDIOGRAM, AND ELECTROCARDIOGRAPH USING THE SAME

(75) Inventor: Daming Wei, The University of Aizu Faculty House A307, 17-26, Matsunaga 1-chome, Ikki-machi, Aizuwakamatsu-shi, Fukushima (JP)

(73) Assignees: Nihon Kohden Corporation, Tokyo (JP); Daming Wei, Fukushima (JP)

(*) Notice: Subject to any disclaimer, the term of this patent is extended or adjusted under 35 U.S.C. 154(b) by 524 days.

(21) Appl. No.: 11/129,421

(22) Filed: May 16, 2005

(65) Prior Publication Data

US 2006/0025695 A1 Feb. 2, 2006

(30) Foreign Application Priority Data

May 14, 2004 (JP) ............................ P2004-144849

(51) Int. Cl.
*A61B 5/04* (2006.01)
(52) U.S. Cl. ..................................... 600/509; 600/512
(58) Field of Classification Search ................. 600/509, 600/512, 513, 523
See application file for complete search history.

(56) References Cited

U.S. PATENT DOCUMENTS

| | | | | |
|---|---|---|---|---|
| 5,058,598 A * | 10/1991 | Nicklas et al. | ............... | 600/512 |
| 5,711,304 A * | 1/1998 | Dower | ......................... | 600/523 |
| 6,119,035 A * | 9/2000 | Wang | .......................... | 600/509 |
| 6,636,761 B2 | 10/2003 | Brodnick | | |
| 6,721,591 B2 | 4/2004 | Wei et al. | | |
| 2002/0045837 A1* | 4/2002 | Wei et al. | ..................... | 600/509 |
| 2002/0087088 A1 | 7/2002 | Brodnick | | |
| 2003/0216655 A1* | 11/2003 | Schreck | ...................... | 600/509 |
| 2004/0024328 A1* | 2/2004 | Tabbara et al. | .............. | 600/523 |
| 2004/0030257 A1 | 2/2004 | Tabbara et al. | | |

FOREIGN PATENT DOCUMENTS

| | | |
|---|---|---|
| JP | 2002-34943 A | 2/2002 |
| JP | 2002-282229 A | 10/2002 |
| WO | 02-011615 A2 | 2/2002 |
| WO | 03-099115 A2 | 12/2003 |

\* cited by examiner

*Primary Examiner*—Mark W Bockelman
*Assistant Examiner*—Roland Dinga
(74) *Attorney, Agent, or Firm*—Sughrue Mion, PLLC

(57) ABSTRACT

In order to derive a standard 12-lead electrocardiogram, ones of limb leads and chest leads which constitute a lead system for the standard 12-lead electrocardiogram using 10 electrodes are selected. Electrocardiographic waveforms corresponding to the selected ones of the limb leads and the chest leads are obtained, as measured electrocardiographic waveforms, with electrodes attached on a living body. Electrocardiographic waveforms corresponding to a remaining ones of the limb leads and the chest leads are calculated, as non-measured electrocardiographic waveforms, with a prescribed transformation matrix and the measured electrocardiographic waveforms.

6 Claims, 3 Drawing Sheets

METHOD FOR DERIVING STANDARD 12-LEAD ELECTROCARDIOGRAM, AND ELECTROCARDIOGRAPH USING THE SAME

BACKGROUND OF THE INVENTION

The present invention relates to a method for deriving a standard 12-lead electrocardiogram effective for diagnosing ischemic heart disease, acute myocardial infarction, or the like, in which a minimum number of electrodes are attached to predetermined areas on the body surface of a living body to thus obtain an electrocardiographic waveform, and focus is placed on an ST segment of the electrocardiographic waveform which will serve as an important index of, in particular, ischemic heart disease. The present invention also relates to an electrocardiograph using such a method.

Conventionally, when an electrocardiogram of a patient is detected, measured, and recorded in a hospital or a like facility, a total of ten electrodes are attached to the body surface of the patient; namely, six positions for chest leads, and four positions for limb leads. Six limb-lead waveforms (I, II, III, aVR, aVL, and aVF) of standard 12-lead waveforms and six chest-lead waveforms (V1, V2, V3, V4, V5, and V6) of the same are derived from electric potentials of the heart detected and measured by the ten electrodes by measuring means, such as an electrocardiograph.

The related-art electrocardiograph or the like can detect, measure, and record an electrocardiogram which is formed from standard 12-lead waveforms and allows appropriate diagnosis and treatment of a variety of heart diseases, through use of ten electrodes. Such a diagnosis and treatment using a plurality of electrodes is possible in a fully-equipped hospital, or the like, where a patient is maintained at rest. However, when at-home or emergency medical treatment is to be performed, no time is available for attaching a large number of electrodes to appropriate positions on the body surface of the living body, from the viewpoint of the status of the patient; moreover, difficulty is encountered in transmitting a large number of lead waveforms in the form of multi-channel signals. In addition, since only one channel (i.e., one lead) or a like number of channels can radio-transmit an electrocardiogram signal, a heart disease is diagnosed through use of, at most, two to four electrodes.

More specifically, conventionally, the following limitations in obtaining a standard, at-rest 12-lead electrocardiogram are pointed out. Namely, (1) attachment of six electrodes to the chest of a patient inhibits a clinician from accessing the chest of the patient; (2) in some cases where a wound is present and/or a bandage is applied onto the chest of the patient, the clinician cannot attach all six chest electrodes; (3) electrodes, wires, and amplifiers required for collecting 12-lead electrocardiogram data over 12 channels increase the overall cost of the apparatus; and (4) the volume of data for representing the 12 channels of 12-lead electrocardiogram data exceeds a maximum capacity; in other words, a transmission bandwidth of a general, typical telemeter unit.

From the above viewpoints, the following configuration has been conventionally practiced as means for detecting and recording an electrocardiogram of standard 12-lead waveforms with a small number of electrodes. For example, four special positions (four electrodes of EASI) on the chest surface of a living body are used, and respective electrocardiographic waveforms thereof are lead. Once signals of the electrocardiographic waveforms have been converted into a vectorcardiogram with use of a fixed coefficient, the thus-converted vectorcardiogram is converted into a 12-lead electrocardiogram. The thus-obtained electrocardiogram is known as an EASI-lead electrocardiogram.

In the lead method of the EASI electrocardiogram of the related art, an approximation to a standard 12-lead electrocardiogram can be attained to a certain degree. However, when leads from the four special positions on the chest surface of the living body are emplaced, appropriate attachment of the electrodes to respective specified positions encounters difficulty, since health care professionals, such as doctors and nurses, are not clinically accustomed to this attachment work, thereby posing a problem of variation arising in detection accuracy of the electrocardiogram. In addition, as described above, when arithmetic operation is performed to acquire the 12-lead electrocardiogram from the electrocardiographic signals derived from the electrodes, the signals must be converted twice (from EASI leads to a vectorcardiogram, and from the vectorcardiogram to a 12-lead electrocardiogram) through use of the fixed coefficient. Accordingly, in some cases variation arises in calculation accuracy. Furthermore, since none of the leads are actually measured values of the 12 leads, some doubts arise with regard to reliability.

General relationships among lead waveforms and measurement positions shown in FIGS. 4A and 4B, and potentials for obtaining a 12-lead electrocardiogram are as follows.

TABLE 1

| I | vL − vR |
|---|---|
| II | vF − vR |
| III | vF − vL |
| aVR | vR − (vL + vF)/2 |
| aVL | vL − (vR + vF)/2 |
| aVF | vF − (vL + vR)/2 |
| V1 | v1 − (vR + vL + vF)/3 |
| V2 | v2 − (vR + vL + vF)/3 |
| V3 | v3 − (vR + vL + vF)/3 |
| V4 | v4 − (vR + vL + vF)/3 |
| V5 | v5 − (vR + vL + vF)/3 |
| V6 | v6 − (vR + vL + vF)/3 |

Accordingly, in the lead method for the EASI lead electrocardiogram of the related art, positions to which the EASI electrodes are attached for measuring respective potentials are special and differ from those of the measurement positions of the lead waveforms of the case shown in Table 1. Therefore, accuracy in positioning to the specified positions in attachment of the electrodes poses considerable influences to a measurement result, which is inconvenient, in that the attachment requires rich experience, and the like. In addition, even when a patient is resting in a fully equipped hospital, or the like, the number of the electrodes used for the standard 12-lead measurement is large. Accordingly, problems arise not only in terms of inconvenience for the patient, but also in terms of increased load on a health care professional who applies the electrodes.

From the above viewpoints, Japanese Patent Publication No. 2002-34943A proposes a method and an electrocardiograph for deriving a standard 12-lead electrocardiogram which enables appropriate diagnosis and treatment of a variety of heart diseases by making use of a lead system subset constituted of the minimum number of leads for obtaining a conventionally-known standard 12-lead electrocardiogram or an M-L leads (Mason-Likar leads) electrocardiogram; and filed a patent application therefor.

Specifically, this method utilizes, as a lead system subset constituted of the minimum number of channels, for instance, leads I and II of limb leads, and leads V1, and V5 or V6 of chest leads which have been used for obtaining the standard 12-lead electrocardiogram. By virtue of the configuration, leads III and aVs (leads aVR, aVL, and aVF) are calculated on the basis of intrinsic relationships among the leads shown in Table 1. The remaining chest leads V2, V3, V4, and V6 or V5 are calculated on the basis of relationships between the potential matrix, the lead vectors and the heart vectors.

A standard 12-lead electrocardiogram obtained as above utilizes the lead system subset of the related-art standard 12-lead electrocardiogram. Therefore, in attachment of the electrodes, positioning to the respective specified positions can be performed easily and without fail without requiring rich experience for the work. Hence, a highly-accurate standard 12-lead electrocardiogram can be derived, thereby enabling appropriate diagnosis and treatment of a variety of heart diseases.

Japanese Patent Publication No. 2002-282229A discloses another method for solving the problem. Specifically, a plurality of electrodes, in a number fewer than ten, are attached to a patient; the respective electrodes are placed at any of 12-lead positions of a standard 10-lead electrodes; electric signals are collected from the electrodes; and a 12-lead electrocardiogram is generated on the basis of the collected electric signals. More specifically, there is disclosed a device which utilizes multiple-linear regression with use of expansion-coefficient equations, to thus arithmetically generate leads in a number fewer than twelve. There is also disclosed that the expansion-coefficient equations are determined on the basis of any of 12-lead electrocardiograms of a hospital's general population, those of a sub-population of the hospital's general population, or those having been previously acquired from the patient.

According to the technique disclosed in Japanese Patent Publication No. 2002-34943A, complicated calculation is required for: calculation of potential matrix and the lead vectors from the minimum leads; estimation of heart vectors on the basis of potential-lead vectors; and further obtaining a standard 12-lead electrocardiogram from the heart vectors.

On the other hand, according to the technique disclosed in Japanese Patent Publication No. 2002-282229A, a standard 12-lead electrocardiogram is obtained by the multiple-linear regression with use of the expansion-coefficient equations. The expansion-coefficient equations are determined by comparing data obtained through uniform sampling of every portion of electrocardiogram at a rate of 120 to 1,000 per second. By such a method, average accuracy can be achieved in derivation of a standard 12-lead electrocardiogram. However, clinically, particularly in ischemic heart disease, acute myocardial infarction, and the like, a change of 0.1 mV in an ST segment of an electrocardiogram is considered to be of pathological significance. Accordingly, as a monitoring diagnostic apparatus for use in pre-hospital care, and the like, emphasis must be placed on accuracy of the ST segment.

SUMMARY OF THE INVENTION

It Is therefore an object of the invention to provide a method and an electrocardiograph for deriving a standard 12-lead electrocardiogram which enables derivation of a standard 12-lead electrocardiogram easily, conveniently and accurately through the use of a minimum number of electrodes; and which is capable of easily and effectively attaining monitoring for appropriate diagnosis and treatment of a variety of heart diseases.

In order to achieve the above object, according to the invention, there is provided a method of deriving a standard 12-lead electrocardiogram, comprising:

selecting ones of limb leads and chest leads which constitute a lead system for the standard 12-lead electrocardiogram using 10 electrodes;

obtaining electrocardiographic waveforms corresponding to the selected ones of the limb leads and the chest leads, as measured electrocardiographic waveforms, with electrodes attached on a living body; and calculating electrocardiographic waveforms corresponding to a remaining ones of the limb leads and the chest leads, as non-measured electrocardiographic waveforms, with a prescribed transformation matrix and the measured electrocardiographic waveforms.

With this configuration, the standard 12-lead electrocardiogram can be derived easily, conveniently, and with high accuracy while avoiding a complicated computing operation. In addition, the method is capable of easily and effectively attaining monitoring for appropriate diagnosis and treatment of a variety of heart diseases. Furthermore, according to the invention, even when some of the electrodes become detached, the measurement-disabled lead can be derived from the remaining leads.

Preferably, the transformation matrix includes information indicative of a relationship between the selected ones of the chest leads and the remaining ones of the chest leads which is obtained in advance from past results of the standard 12-lead electrocardiogram using 10 electrodes.

Here, it is preferable that the relationship is an average relationship which is obtained from the past results of one specific person or any plurality of persons.

Here, it is further preferable that the relationship is obtained such that an ST segment of an electrocardiogram has the best accuracy in the calculated electrocardiographic waveforms.

It is also preferable that the relationship is obtained by a least squares method.

With the above configurations, a highly-accurate derivation method is provided when an emergency response is required as in cases of ischemic heart disease, acute myocardial infarction, and the like, at a site of pre-hospital care, and the like. When an average relationship of a plurality of past time points with regard to a specific person is used, the specific person's own data are used. Accordingly, considerably favorable coincidence can be obtained, along with a highly-accurate result. Meanwhile, when an average relationship of an indefinite number of persons is used for a case of emergency, such as in an ambulance, a stable result can be obtained without including a large error in accuracy.

According to the invention, there is also provided an electrocardiograph for deriving a standard 12-lead electrocardiogram, comprising:

a plurality of electrodes, adapted to be attached on portions of a living body corresponding to selected ones of limb leads and chest leads which constitute a lead system for the standard 12-lead electrocardiogram using 10 electrodes;

a processor, which calculates electrocardiographic waveforms corresponding to a remaining ones of the limb leads and the chest leads, as non-measured electrocardiographic waveforms, with a prescribed transformation matrix and electrocardiographic waveforms corresponding to the selected ones of the limb leads and the chest leads which are obtained with the electrodes as measured electrocardiographic waveforms; and a display, which displays the measured electrocardiographic waveforms and the non-measured electrocardiographic waveforms.

With this configuration, a health care professional can carry out a diagnosis while recognizing whether each lead of derived 12 leads is a lead having been detected and measured or a lead obtained by calculation. Accordingly, reliability with respect to a waveform of each lead can be judged easily. Therefore, there can be obtained an electrocardiograph that provides a highly-accurate standard 12-lead electrocardiogram which enables appropriate diagnosis and treatment of a variety of heart diseases even when measurement of the standard 12-lead electrocardiogram is difficult as in cases of bedside monitoring in an ICU, CCU, or the like in a hospital, or the like; home monitoring; emergency monitoring; exercise monitoring; and the like.

BRIEF DESCRIPTION OF THE DRAWINGS

The above objects and advantages of the present invention will become more apparent by describing in detail preferred exemplary embodiments thereof with reference to the accompanying drawings, wherein.

DETAILED DESCRIPTION OF THE EMBODIMENTS

Figure 1:
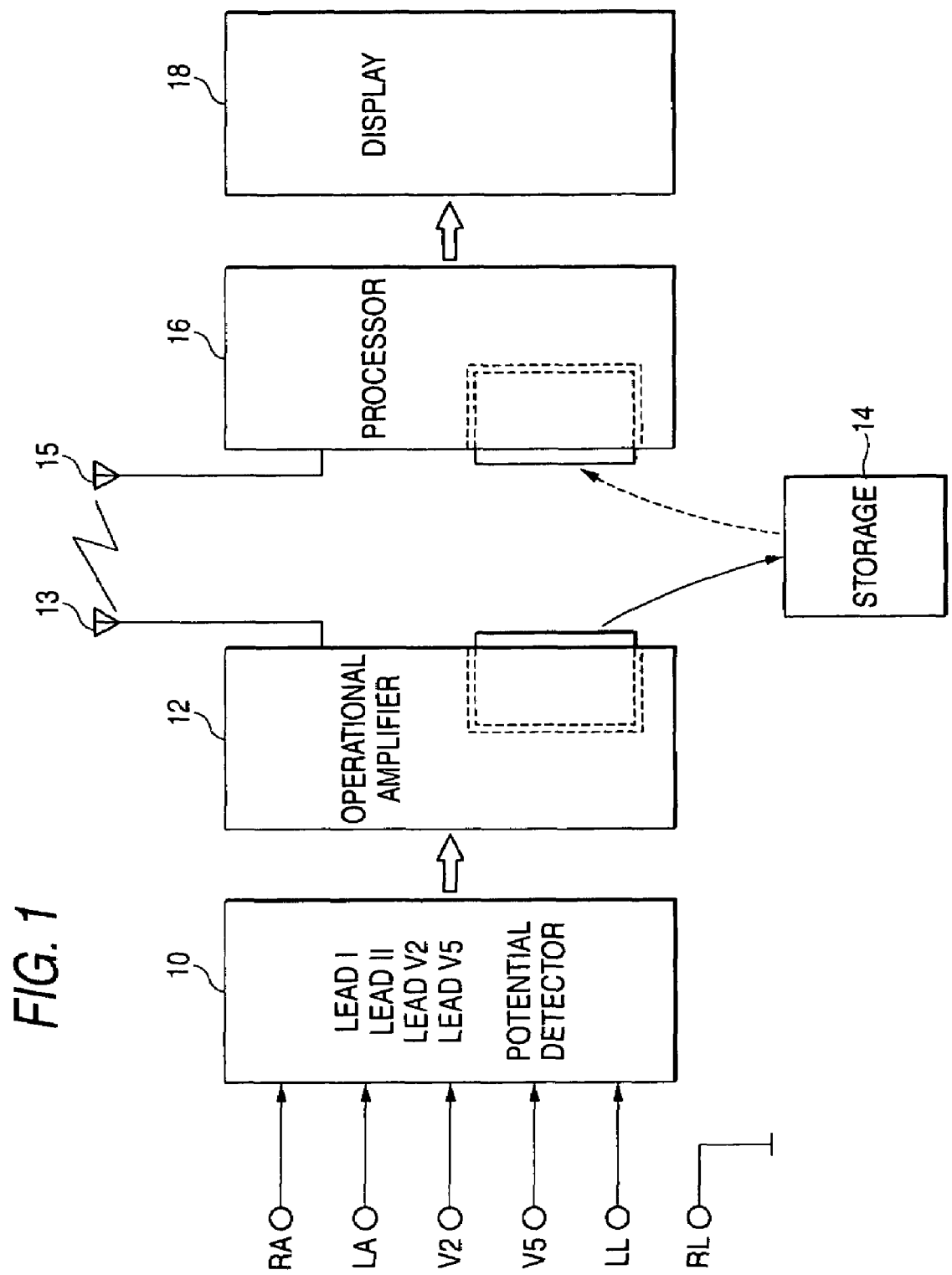
FIG. 1 is a block diagram showing a system configuration of an electrocardiograph according to one embodiment of the invention.

Embodiments of the invention will be described below in detail with reference to the accompanying drawings.

A rationale for deriving a standard 12-lead electrocardiogram according to the invention is as follows. A total of six electrodes are attached to a body surface of a living body for obtaining lead waveforms from a lead system subset which is constituted of two leads from limb leads (e.g., leads I and II) and two leads from chest leads (e.g., leads V2, V5). On the basis of electrocardiographic data detected and measured by these electrodes, the remaining four chest leads (e.g., leads V1, V3, V4, and V6), which are not measured by electrodes, can be calculated by subjecting data on the above-mentioned four leads to a transformation matrix constituted of a derivation matrix of the following equation (1).

$$\begin{bmatrix} V1 \\ V3 \\ V4 \\ V6 \end{bmatrix} = \begin{bmatrix} \alpha_{I-1}\alpha_{II-1} & \alpha_{2-1}\alpha_{5-1} \\ \alpha_{I-3}\alpha_{II-3} & \alpha_{2-3}\alpha_{5-3} \\ \alpha_{I-4}\alpha_{II-4} & \alpha_{2-4}\alpha_{5-4} \\ \alpha_{I-6}\alpha_{II-6} & \alpha_{2-6}\alpha_{5-6} \end{bmatrix} \begin{bmatrix} I \\ II \\ V2 \\ V5 \end{bmatrix} \quad (1)$$

In this case, as is apparent from Equation (1), when all eight of the. electrocardiographic data sets (leads I, II, V1, V2, V3, V4, V5, and V6) are obtained, relationships with regard to the remaining leads of the derivation matrix serving as the transformation matrix for calculating the non-measurement electrocardiographic data can be obtained by means arbitrarily setting the measurement leads.

More specifically, the derivation matrix serving as the transformation matrix can be determined in advance on the basis of the eight electrocardiogram data sets having been collected by the lead system with ten electrodes of a standard 12-lead electrocardiogram. In this case, preferable sources from which the electrocardiogram data are collected are, for instance, an average value obtained by applying a least squares method to electrocardiographic data on a plurality of past time points of a specific person or those of an any plurality of persons.

A standard 12-lead electrocardiogram according to the embodiment can be derived on the basis of the above-mentioned basic principle. More specifically, in a case where the leads I and II are detected, electrodes for detecting limb leads of a standard 12-lead electrocardiogram are disposed at four positions constituted of the right and left arms (electrodes L, R) and the right and left lower limbs (electrodes LL, RL). Meanwhile, in a case of an exercise stress test, or the like, the Mason-Likar modification of the standard 12-lead electrocardiogram is taken as limb leads of modified 12-leads; and electrodes are disposed at four positions constituted of the lateral distal ends of the clavicles (electrodes L, R) as the right and left upper limbs, and right and left flank positions (electrodes LL, RL) as the right and left lower limbs. Meanwhile, the electrode RL is caused to serve as a grounding electrode. Thus, from the electrodes for measurement of the limb leads, electrocardiographic lead waveforms of the leads I and II of the standard 12-lead electrocardiogram can be detected and measured.

Meanwhile, more than two electrodes are disposed for measurement of chest leads of the standard 12-lead electrocardiogram. In this case, a lead position where derivation accuracy of the lead is the highest is preferably selected as the chest lead among six leads consisting of V1 to V6. Selection of a lead position of highest derivation accuracy for setting the measurement electrode also relates to the derivation matrix serving as the transformation matrix for calculating the non-measurement electrocardiographic data by Equation (1).

For example, electrodes for detecting electrocardiographic signals from two leads (V2, V5) serving as the portion of lead potentials, are disposed at two positions constituted of, for instance, the left margin of sternum in the fourth rib interspace (for obtaining electrocardiographic signals of V2) and an intersecting point of the left anterior axillary line and a horizontal line crossing the fifth intercostal space (for obtaining electrocardiographic signals of V5).

Figure 2:
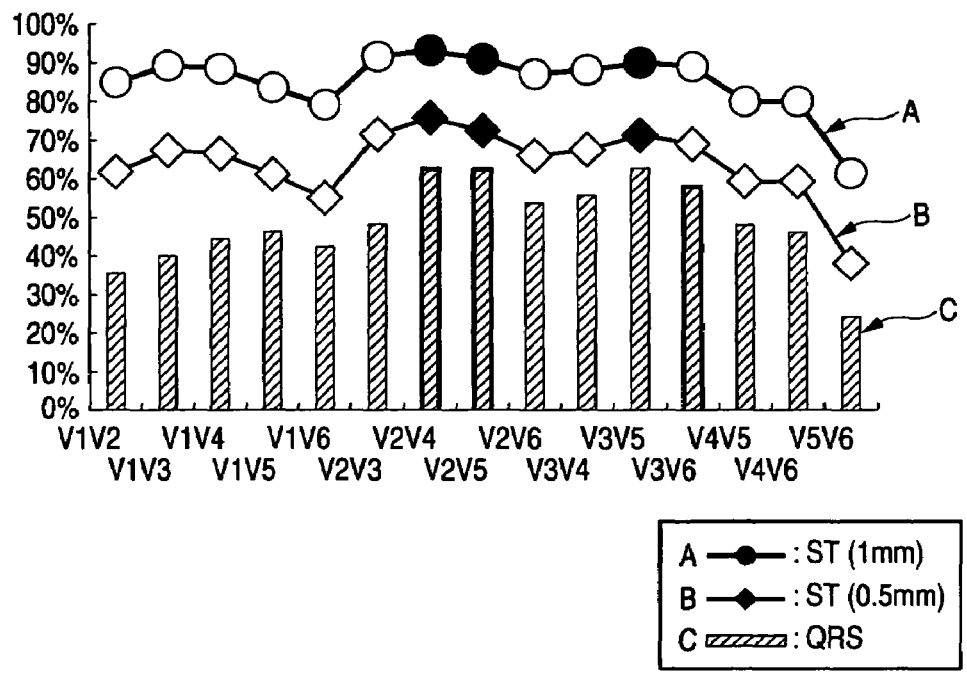
FIGS. 2 and 3 are graphs for explaining data accuracy obtained by the electrocardiograph.

Accordingly, with regard to all 15 possible combinations of electrodes related to the chest lead, respective derivation matrices serving as the transformation matrices were obtained with use of a standard 12-lead electrocardiogram of a normal health control; and derivation accuracies of the respective lead waveforms were obtained by comparing the measured values and calculated values. FIG. 2 shows the results.

Figure 5:
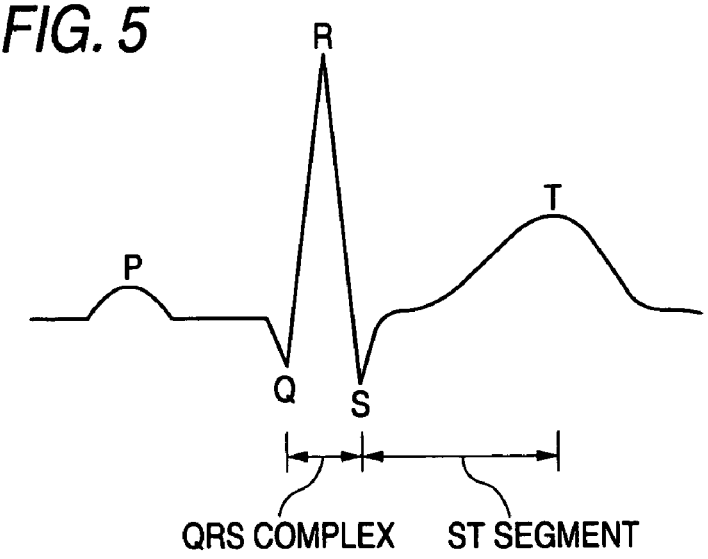
FIG. 5 is a diagram showing waveforms of a P wave, a QRS complex and a T wave in a general electrocardiogram.

In FIG. 2, an ST segment and QRS complex of a calculation-derived electrocardiogram waveform as shown in FIG. 5 are evaluated as compared with measured waveform. With regard to the ST segment, a ratio of number of electrocardiograms where a difference in ST level between a measured waveform and a calculation-derived waveform was 1 mm or smaller to the total number of electrocardiograms used for evaluation (see a characteristic line A); and a ratio of number of electrocardiograms where the difference in ST level was 0.5 mm or smaller to the total number of electrocardiograms used for evaluation (see a characteristic line B); and with regard to the QRS complex, a ratio of number of electrocardiograms, where a correlation coefficient of the QRS complex between the measured waveform and the calculation-derived waveform was 0.8 or larger and where an amplitude error fell within a range of 50% to the total number of electrocardiograms used for evaluation (see a characteristic bar graph C) are shown in the graphs.

As a result, as is apparent in FIG. 2, combinations of the leads V2 and V4, V2 and V5, and V3 and V5 were confirmed to exhibit the highest derivation accuracy in any one of the characteristics. In addition, for determination of the derivation matrix serving as the transformation matrix, it was confirmed that the highest derivation accuracy is obtained when attention is focused on the ST segment of the electrocardiogram.

Figure 3:
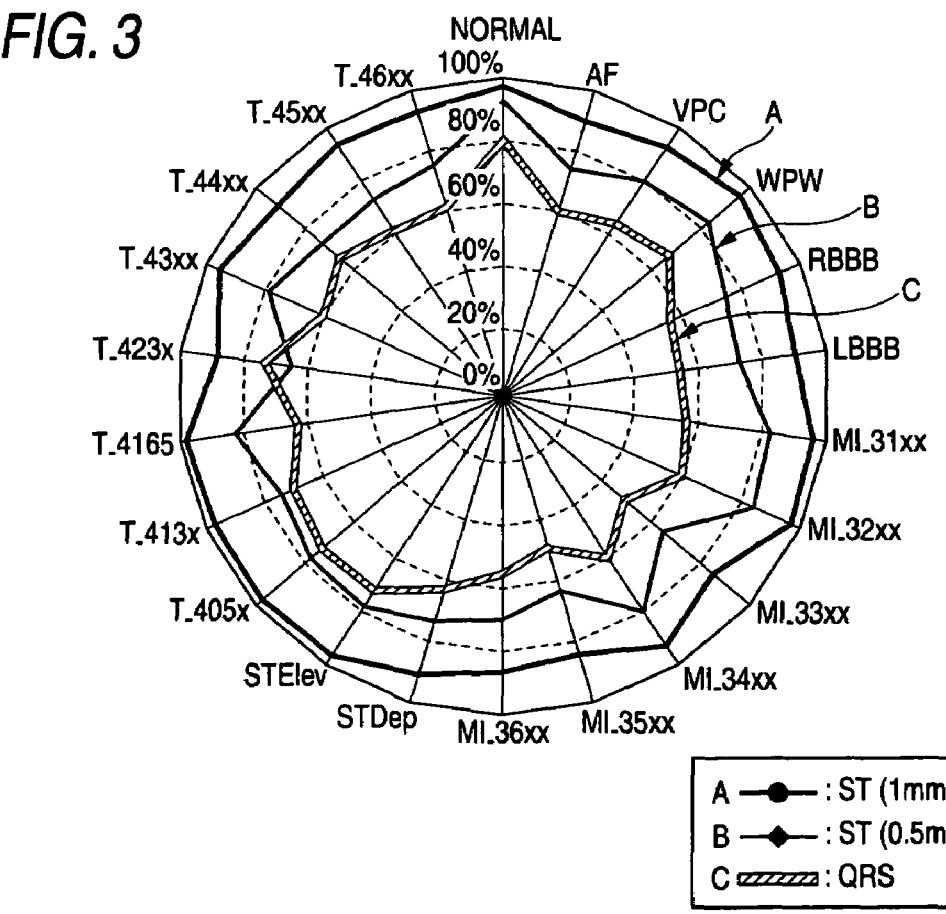
Figure 4A:
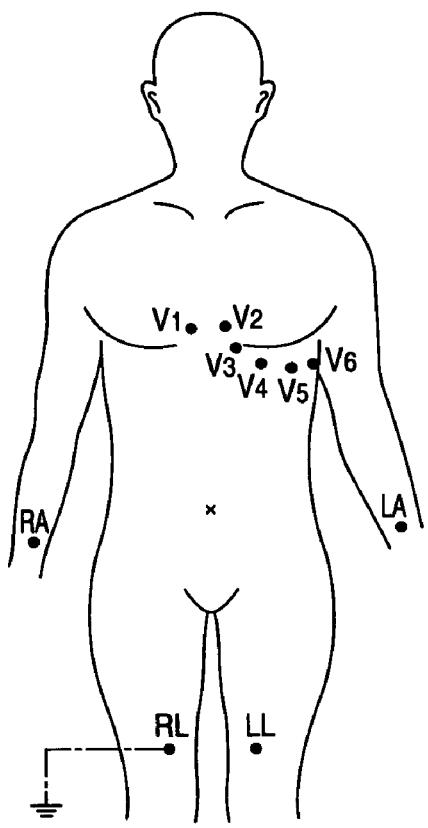
FIGS. 4A and 4B are diagrams showing examples of lead electrode positions for deriving a standard 12-lead electrocardiogram.
Figure 4B:
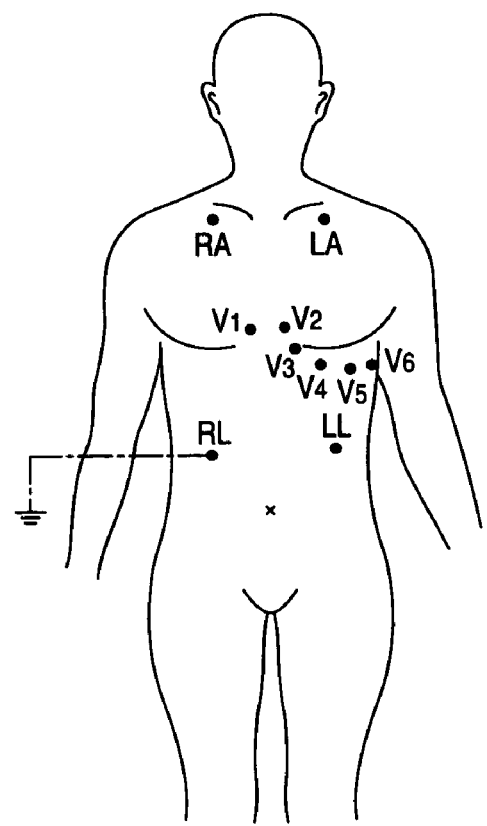

Next, with use of measurement electrodes constituted of the combination of the leads V2 and V4 having the high derivation accuracy, evaluation for each category was conducted while using, as an evaluation database, electrocardiogram data on about 10,000 examples having been classified into 22 categories, wherein attention was focused on the ST segment and the QRS complex of the electrocardiogram as in the case of the above. FIG. 3 shows the results.

The results also reveal that the highest derivation accuracy was obtained when attention was focused on the ST segment of the electrocardiogram for determination of the derivation matrix serving as the transformation matrix.

In a electrocardiograph of the invention shown in FIG. 1, a potential detector 10 is configured so as to detect and measure, for instance, potentials between two leads of limb leads (e.g., the leads I and II) and two leads of chest leads (e.g., the leads V2 and V5) by respective electrodes (RA, LA, RL, and LL, and V2 and V5) disposed on the body surface of a living body. An operational amplifier 12 is configured to derive respective lead waveform data (e.g., the leads I, II, V2, and V5) as a lead system subset of the standard 12-lead electrocardiogram.

The electrocardiograph is configured such that the respective lead waveform data derived from the operation amplifier 12 are transmitted by way of unillustrated wireless transmitter including antennas 13, 15 to a processor 16. Alternatively, the electrocardiograph can also be configured as follows. The respective lead waveform data derived from the operation amplifier 12 are stored in a storage 14 which is installed in the processor 16, and the stored respective lead waveform data are read out therefrom.

Accordingly, in the processor 16, the respective waveforms of leads having been excluded from the lead system subset (e.g., the leads V1, V3, V4, and V6) are calculated in accordance with the method for deriving the standard 12-lead electrocardiogram according to the present invention with use of Equation (1). Thereafter, standard 12-lead electrocardiographic data (leads I, II, V1, V2, V3, V4, V5, and V6) obtained by the processor 16 are displayed by a display 18. In relation to the above, the lead waveform data measured by the lead system subset and the lead waveform data derived by the calculation may be displayed so as to be visually distinguished.

In addition, the leads III and aVs (leads aVR, aVL, and aVF) can be calculated in accordance with the intrinsic relationships between the leads shown in Table 1. Therefore, there can be realized a configuration wherein the limb leads, which can be obtained in the above manner, are also calculated by the processor 16, and thereafter displayed by the display 18.

Furthermore, in a normal, standard 12-lead electrocardiograph, the following configuration is applicable. An electrode-detachment detector is disposed in the potential detector 10. Upon detachment of any of all the electrodes, the detachment is detected, to thus derive the standard 12-lead electrocardiogram by calculating the measurement-disabled leads from the remaining leads under measurement in accordance with the derivation method of the invention. At this time, which electrode has detached may be displayed on a display screen; and the measured lead waveform data and the lead waveform data derived by the calculation may be displayed so as to be visually distinguished.

Accordingly, the electrocardiograph of the above configuration is capable of attaining appropriate and effective monitoring of a standard 12-lead electrocardiogram even when measurement of the standard 12-lead electrocardiogram is difficult in such cases as at a bedside in an ICU, CCU, or the like in a hospital, or the like; during home care; during emergency treatment; and during exercise.

Hithertofore, a configuration including use of a radio telemeter has been described as the preferred embodiment of the invention. However, the method and apparatus according to the invention are not limited thereto, and remain effective when including use of, for instance, a line transmission system. Furthermore, the method and apparatus may be modified, altered, and changed in various manners within the scope of the invention.

What is claimed is:

1. A method of deriving a standard 12-lead electrocardiogram, comprising:
   selecting ones of limb leads and chest leads which constitute a lead system for the standard 12-lead electrocardiogram using 10 electrodes;
   obtaining electrocardiographic waveforms corresponding to the selected ones of the limb leads and the chest leads, as measured electrocardiographic waveforms, with electrodes attached on a living body; and
   calculating electrocardiographic waveforms corresponding to a remaining ones of the limb leads and the chest leads, as non-measured electrocardiographic waveforms, with a single prescribed transformation matrix and the measured electrocardiographic waveforms;
   wherein the transformation matrix includes information indicative of a relationship between the selected ones of the chest leads and the remaining ones of the chest leads which is obtained in advance from past results of the standard 12-lead electrocardiogram using 10 electrodes; and
   wherein the relationship is an average relationship which is obtained from the past results of one specific person or any plurality of persons.

2. The derivation method as set forth in claim 1, wherein the relationship is obtained such that an ST segment of an electrocardiogram has the best accuracy in the calculated electrocardiographic waveforms.

3. The derivation method as set forth in claim 1, wherein the relationship is obtained by a least squares method.

4. An electrocardiograph for deriving a standard 12-lead electrocardiogram, comprising:
   a plurality of electrodes, adapted to be attached on portions of a living body corresponding to selected ones of limb leads and chest leads which constitute a lead system for the standard 12-lead electrocardiogram using 10 electrodes;
   a processor, which calculates electrocardiographic waveforms corresponding to a remaining ones of the limb leads and the chest leads, as non-measured electrocardiographic waveforms, with a single prescribed transformation matrix and electrocardiographic waveforms corresponding to the selected ones of the limb leads and the chest leads which are obtained with the electrodes as measured electrocardiographic waveforms; and
   a display, which displays the measured electrocardiographic waveforms and the non-measured electrocardiographic waveforms; wherein:

the transformation matrix includes information indicative of a relationship between the selected ones of the chest leads and the remaining ones of the chest leads which is obtained in advance from past results of the standard 12-lead electrocardiogram using 10 electrodes; and the relationship is an average relationship which is obtained from the past results of one specific person or any plurality of persons.

5. The electrocardiograph as set forth in claim 4, wherein the relationship is obtained such that an ST segment of an electrocardiogram has the best accuracy in the calculated electrocardiographic waveforms.

6. The electrocardiograph as set forth in claim 4, wherein the relationship is obtained by a least squares method.

* * * * *